United States Patent [19]

Anzai et al.

[11] Patent Number: 5,707,768

[45] Date of Patent: Jan. 13, 1998

[54] DIAMINE COMPOUNDS AND ELECTROPHOTOGRAPHIC PHOTORECEPTOR

[75] Inventors: Mitsutoshi Anzai; Atsushi Takesue; Takanobu Watanabe; Chieko Inayoshi, all of Tsukuba, Japan

[73] Assignee: Hodogaya Chemical Co., Ltd., Kawasaki, Japan

[21] Appl. No.: 563,823

[22] Filed: Nov. 28, 1995

[30] Foreign Application Priority Data

Nov. 30, 1994 [JP] Japan .................. 6-319477

[51] Int. Cl.⁶ .................. G03G 5/06; G03G 5/09
[52] U.S. Cl. .................. 430/71; 430/56; 430/59; 430/72; 430/73; 430/74; 430/75; 430/76; 430/77; 430/78; 430/79; 430/81; 430/82
[58] Field of Search .................. 430/73, 72, 74, 430/71, 59, 56, 75, 76, 77, 78, 79, 81, 82

[56] References Cited

U.S. PATENT DOCUMENTS 3,860,568  1/1975  Chabert et al. .................. 526/141
4,544,718  10/1985  Yeh et al. .................. 526/141

FOREIGN PATENT DOCUMENTS 62-201447  5/1987  Japan .................. 430/76
3-273258  12/1991  Japan .................. 430/73

OTHER PUBLICATIONS

Patent & Trademark Office English-Language Translation of JP 4-321649 (Pub. Nov. 11, 1992).

*Primary Examiner*—Janis L. Dote
*Attorney, Agent, or Firm*—Oblon, Spivak, McClelland, Maier & Neustadt, P.C.

[57] ABSTRACT

A diamine compound of the following formula (1):

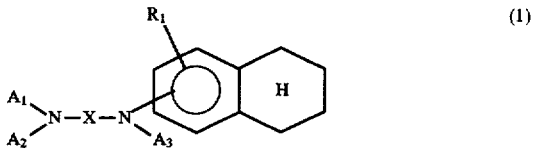

wherein $R_1$ is a hydrogen atom, a lower alkyl group or a lower alkoxy group, each of $A_1$, $A_2$ and $A_3$ which are independent of one another, is a substituted or unsubstituted alkyl group, a substituted or unsubstituted aryl group, or a group of the following formula (2):

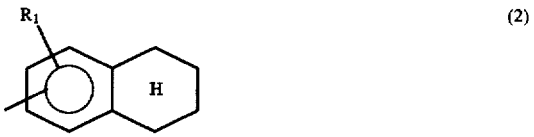

wherein $R_1$ is as defined above, and X is a substituted or unsubstituted arylene group or a substituted or unsubstituted heterocyclic bivalent group.

7 Claims, 2 Drawing Sheets

DIAMINE COMPOUNDS AND ELECTROPHOTOGRAPHIC PHOTORECEPTOR

BACKGROUND OF THE INVENTION

FIELD OF THE INVENTION

The present invention relates to novel diamine compounds and a electrophotographic photoreceptor having a photosensitive layer containing such a diamine compound.

DISCUSSION OF BACKGROUND

The electrophotographic system is one of image-forming methods, wherein the surface of a photoreceptor employing a photoconductive material is electrified, for example, by corona discharge and subjected to exposure to selectively dissipate the charge at the exposed portion to obtain an electrostatic latent image, which is then developed by a toner, and transferred to e.g. a paper sheet, followed by fixing to obtain an image.

The photoreceptor may be an inorganic photoreceptor composed mainly of an inorganic photoconductive compound such as selenium, zinc oxide, cadmium sulfide or silicon, or an organic photoreceptor employing an organic compound having a charge-generating material and a low molecular weight or high molecular weight charge-transporting material dispersed in a binder resin. Inorganic photoreceptors have many merits respectively and have been widely used. However, for example, selenium has drawbacks such that the production conditions are difficult, the production costs are high, and it is weak against heat or mechanical shock and likely to undergo crystallization, whereby the properties tend to deteriorate. Zinc oxide and cadmium sulfide have a problem with respect to the moisture resistance or mechanical strength and have a drawback that they undergo deterioration due to exposure or electrification of a dye incorporated as a sensitizer, whereby no adequate durability can be obtained. Also silicon has problems that the production conditions are difficult, and the production costs are high since highly irritating gas is used, and since it is sensitive to humidity, its handling requires a special care.

In recent years, for the purpose of overcoming such drawbacks inherent to these inorganic photoreceptors, organic photoreceptors employing various organic compounds have been studied and widely used. The organic photoreceptor includes a single layer type photoreceptor having a charge-generating material and a charge-transporting material dispersed in a binder resin and a laminated layer type photoreceptor having a charge-generating layer and a charge-transporting layer laminated to have separate functions. The function-separated type organic photoreceptor has been extensively studied and widely used for such reasons that a wide range of choice of the respective materials is available, and a photoreceptor having optional performance can relatively easily be prepared by a proper combination.

As the charge-generating material, many organic pigments or dyes have been proposed and practically used, including, for example, azo compounds, bisazo compounds, trisazo compounds, tetrakis azo compounds, thiapyrylium salts, squarilium salts, azulenium salts, cyanine dyes, perylene compounds, non-metal or metal phthalocyanine compounds, polycyclic quinone compounds, thioindigo compounds, and quinacridone compounds.

The charge-transporting material includes, for example, oxadiazole compounds disclosed in Japanese Examined Patent Publication No. 5466/1959, oxazole compounds disclosed in Japanese Unexamined Patent Publication No. 123544/1981, pyrazoline compounds disclosed in Japanese Examined Patent Publication No. 41880/1977, hydrazone compounds disclosed in Japanese Examined Patent Publications No. 42380/1980, No. 40104/1986, No. 35673/1987 and No. 35976/1988, diamine compounds disclosed in Japanese Examined Patent Publication No. 32372/1983, stilbene compounds disclosed in Japanese Examined Patent Publications No. 18738/1988, No. 19867/1988 and No. 39306/1991, and butadiene compounds disclosed in Japanese Unexamined Patent Publication No. 30255/1987. Organic photoreceptors employing these charge-transporting materials have excellent properties, and some of them are practically used. However, there has been none which fully satisfies various properties required for a photoreceptor for an electrophotographic system.

The charge-transporting material to be used for the organic photoreceptor, is required to satisfy various properties as a photoreceptor including the sensitivity and to have chemical stability so that it is durable against light, ozone or an electrical load as well as stability and durability so that the sensitivity will not deteriorate by repeated use or use for a long period of time.

SUMMARY OF THE INVENTION

It is an object of the present invention to provide a compound useful as such a charge-transporting material.

Another object of the present invention is to provide a electrophotographic photoreceptor which satisfies the properties required for a photoreceptor and which has high sensitivity and high durability.

The present invention provides a diamine compound of the following formula (1):

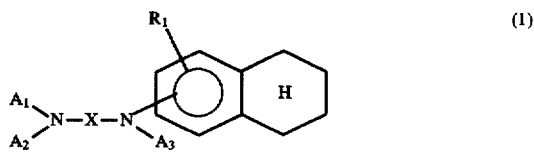

wherein $R_1$ is a hydrogen atom, a lower alkyl group or a lower alkoxy group, each of $A_1$, $A_2$ and $A_3$ which are independent of one another, is a substituted or unsubstituted alkyl group, a substituted or unsubstituted aryl group, or a group of the following formula (2):

wherein $R_1$ is as defined above, and X is a substituted or unsubstituted arylene group or a substituted or unsubstituted heterocyclic bivalent group.

Further, the present invention provides a electrophotographic photoreceptor having a photosensitive layer which contains a diamine compound as defined above.

DETAILED DESCRIPTION OF THE PREFERRED EMBODIMENTS

Figure 1:
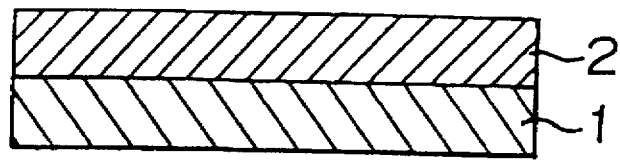
FIG. 1 is a cross-sectional view of a single layer electrophotographic photoreceptor.

In the present invention, the diamine compound of the above formula (1) to be incorporated in a photosensitive layer is a novel compound. Such a compound can be synthesized by a condensation reaction of a corresponding dihalogen compound with a corresponding diarylamine, or by a sequential condensation reaction of a corresponding diamino compound with a corresponding aryl halide. These condensation reactions are known as a Ullmann reaction.

The diamine compound of the formula (1) of the present invention can be obtained, for example, by a process wherein a diarylamine compound of the following formula (3):

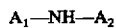   (3)

wherein $A_1$ and $A_2$ are as defined above with respect to the formula (1) is reacted with a large excess amount of a dihalogen compound of the following formula (4):

   (4)

wherein Z is a chlorine atom, a bromine atom or an iodine atom, and X is as defined above with respect to the formula (1), for condensation to obtain a monohalogenated amino compound of the following formula (5):

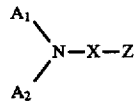   (5)

wherein $A_1$ and $A_2$ are as defined above with respect to the formula (1), and Z is as defined above with respect to the formula (4), which is further reacted with an amino compound of the following formula (6):

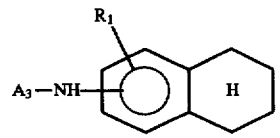   (6)

wherein $R_1$ and $A_3$ are as defined above with respect to the formula (1), for condensation.

Or, the diamine compound of the formula (1) of the present invention can be obtained by a process wherein the above-mentioned dihalogen compound of the following formula (4):

   (4)

wherein X and Z are as defined above, is reacted with two mols of the above-mentioned amino compound of the following formula (6):

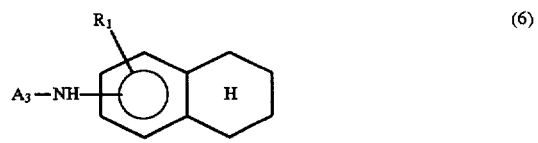

wherein $R_1$ and $A_3$ are as defined above, for condensation.

Otherwise, the diamine compound of the formula (1) of the present invention can be obtained by a process in which a diamino compound of the following formula (7):

   (7)

wherein X is as defined above, is acetylated to obtain an N,N'-diacetyl compound of the following formula (8):

   (8)

wherein X is as defined above, which is then reacted with two mols of a halogenated tetrahydronaphthalene compound of the following formula (9):

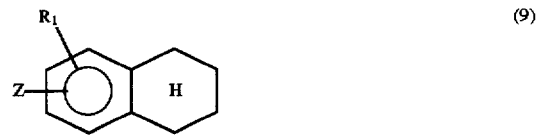   (9)

wherein $R_1$ and Z are as defined above, for condensation, followed by hydrolysis to obtain an N,N'-bis(tetrahydronaphthyl)diamino compound of the following formula (10):

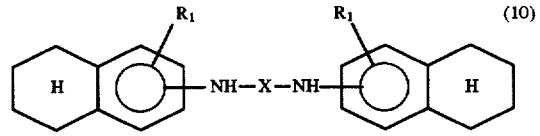   (10)

wherein $R_1$ and X are as defined above, which is further condensed with two mols of a halogen compound of the following formula (11):

   (11)

wherein $A_3$ and Z are as defined above.

The above sequential condensation reaction may be carried out in such an order that after the diacetylation of the compound of the formula (7), the compound of the formula (11) is reacted, followed by hydrolysis and then by a reaction with the compound of the formula (9), to obtain the diamine compound of the formula (1) of the present invention.

The above-described condensation reaction of the diarylamine compound with the halogenated tetralin compound is a reaction known as an Ullmann reaction, which is carried out in the presence or absence of a solvent. As the solvent, a high boiling point solvent such as nitrobenzene, dichlorobenzene or dimethylsulfoxide, may be employed. Further, as a basic compound, potassium carbonate, sodium carbonate, sodium hydrogencarbonate, potassium hydroxide or sodium hydroxide may, for example, be employed. Further, the reaction is usually conducted by means of a catalyst such as a copper powder or a copper halide. The reaction temperature is usually from 160° to 230° C.

In the above formula (1), when $R_1$ is a lower alkyl group or a lower alkoxy group, such a lower alkyl group or a lower alkoxy group is preferably a $C_{1-4}$ alkyl group or a $C_{1-4}$ alkoxy group, respectively.

In the above formula (1), when $A_1$, $A_2$ or $A_3$ is a substituted alkyl group, the substituent may, for example, be a $C_{1-4}$ lower alkoxy group, a $C_{5-6}$ cycloalkyl group, a benzyl group, a phenyl group or a halogen atom. When the substituent is a lower alkoxy group, it may further be substituted by a $C_{1-4}$ lower alkoxy group or a halogen atom. When the substituent is a benzyl group or a phenyl group, it may further be substituted by a $C_{1-4}$ lower alkyl group, a $C_{1-4}$ lower alkoxy group or a halogen atom. Further, the alkyl group for each of $A_1$, $A_2$ and $A_3$ may, for example, be a $C_{1-8}$ straight chain or branched chain alkyl group.

In the above formula (1), when $A_1$, $A_2$ or $A_3$ is a substituted aryl group, the substituent may, for example, be a $C_{1-4}$ lower alkyl group, a $C_{1-4}$ lower alkoxy group, a $C_{5-6}$ cycloalkyl group, a benzyl group, a phenyl group or a halogen atom. When the substituent is a lower alkyl group or a lower alkoxy group, it may further be substituted by a $C_{1-4}$ lower alkoxy group or a halogen atom. When the substituent is a benzyl group or a phenyl group, it may further be substituted by a $C_{1-4}$ lower alkyl group, a $C_{1-4}$ lower alkoxy group or a halogen atom. Further, the aryl group for each of $A_1$, $A_2$ and $A_3$ may, for example, be a phenyl group, a naphthyl group, a biphenylyl group, an anthryl group or a pyrenyl group.

In the above formula (1), when X is an arylene group, the arylene group may, for example, be phenylene, biphenylene, terphenylene, naphthylene, anthrylene, phenanthrylene, fluorene-diyl or a group of the following formula (12) which may have a substituent:

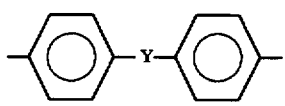
(12)

wherein Y is —O—, —S—, —SO$_2$—, —CH=CH—, —CH$_2$—, —CH$_2$CH$_2$—, —OCH$_2$O—, —OCH$_2$CH$_2$CH$_2$O—,

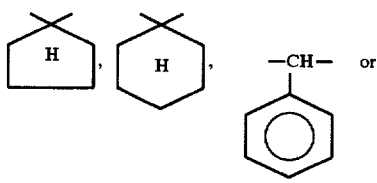

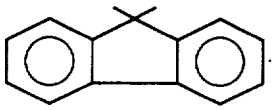

When X is a heterocyclic bivalent group, the heterocyclic ring may, for example, be oxadiazole, thiadiazole, benzofuran, benzothiophene, benzoxazole, benzothiazole, dibenzofuran, dibenzothiophene, carbazole, acridine, phenazine, phenoxazine or phenothiazine.

Further, when X is a substituted arylene or heterocyclic bivalent group, the substituent may be the same as the above-mentioned substituent for the substituted aryl group for each of $A_1$, $A_2$ and $A_3$ in the formula (1).

Among the compounds of the present invention, the following compounds are particularly preferred:

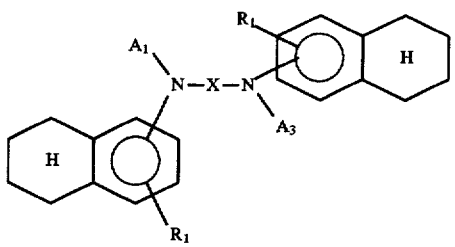

wherein $R_1$, $A_1$, $A_3$ and X are as defined above;

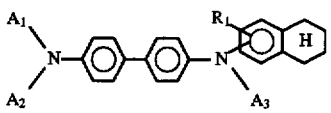

wherein $R_1$, $A_1$, $A_2$ and $A_3$ are as defined above;

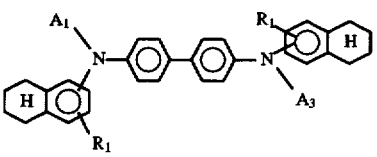

wherein $R_1$, $A_1$ and $A_3$ are as defined above; and

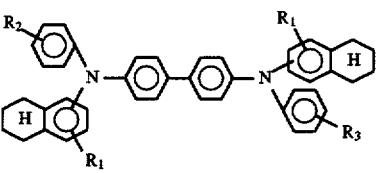

wherein $R_1$ is as defined above, and each of $R_2$ and $R_3$ which are independent of each other, is a hydrogen atom, a $C_{1-4}$ alkyl group or a $C_{1-4}$ alkoxy group.

The following compounds may be mentioned as specific examples of the diamine compound of the formula (1) to be incorporated in the photosensitive layer of the present invention.

TABLE 1

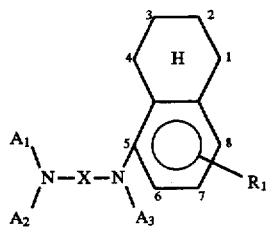

| Comp. No. | X | A₁ | A₂ | A₃ | R₁ |
|---|---|---|---|---|---|
| 1-1 | 1,3-phenylene | phenyl | 3-chlorophenyl | 3-chlorophenyl | H |
| 1-2 | 1,3-phenylene | phenyl | 4-methylphenyl | 4-methylphenyl | H |
| 1-3 | 1,3-phenylene | phenyl | 2,4-dimethylphenyl | 2,4-dimethylphenyl | H |
| 1-4 | 1,3-phenylene | 4-ethoxyphenyl | 4-ethoxyphenyl | 4-ethoxyphenyl | H |
| 1-5 | 3,5-dimethyl-1,3-phenylene | 3-methylphenyl | 3-methylphenyl | phenyl | 8-CH₃ |
| 1-6 | 1,4-phenylene | phenyl | —C₂H₅ | —C₂H₅ | H |
| 1-7 | 1,4-phenylene | phenyl | H | H | H |
| 1-8 | 1,4-phenylene | phenyl | —CH₂-phenyl | —CH₂-phenyl | H |
| 1-9 | 1,4-phenylene | phenyl | phenyl | phenyl | 8-CH₃ |
| 1-10 | 2,4,6-trimethyl-1,3-phenylene | 3-methylphenyl | 3-methylphenyl | phenyl | H |

TABLE 1-continued
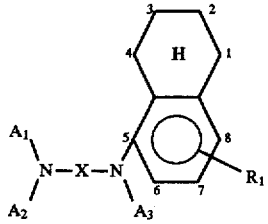
| Comp. No. | X | A₁ | A₂ | A₃ | R₁ |
|---|---|---|---|---|---|
| 1-11 | 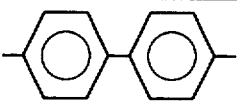 |  | —CH₂ | —CH₂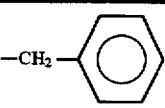 | H |
| 1-12 |  |  |  (Cl) |  (Cl) | H |
| 1-13 | 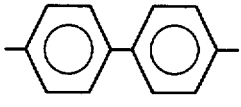 | 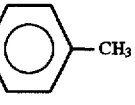—CH₃ |  (CH₃) |  (CH₃) | H |
| 1-14 | 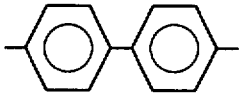 | 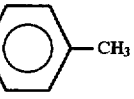—CH₃ | 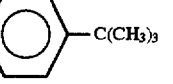—C(CH₃)₃ | 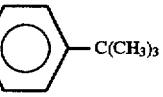—C(CH₃)₃ | H |
| 1-15 |  |  | 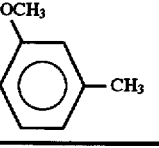 (OCH₃, CH₃) |  | H |
TABLE 2
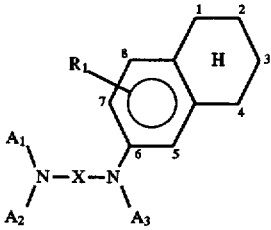
| Comp. No. | X | A₁ | A₂ | A₃ | R₁ |
|---|---|---|---|---|---|
| 2-1 | 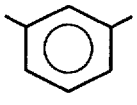 | 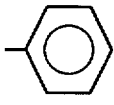 | 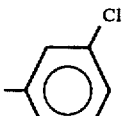 (Cl) | 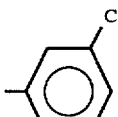 (Cl) | H |
| 2-2 | 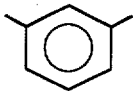 | 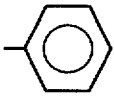 | 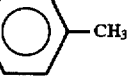—CH₃ | 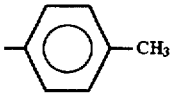—CH₃ | H |

TABLE 2-continued

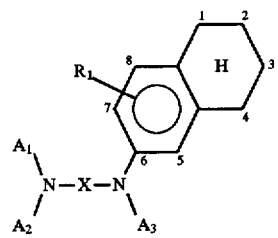

| Comp. No. | X | A₁ | A₂ | A₃ | R₁ |
|---|---|---|---|---|---|
| 2-3 | m-phenylene | phenyl | 2,4-dimethylphenyl | 2,4-dimethylphenyl | H |
| 2-4 | m-phenylene | 4-OC₂H₅-phenyl | 4-OC₂H₅-phenyl | 4-OC₂H₅-phenyl | H |
| 2-5 | 3,5-dimethylphenylene | 4-CH₃-phenyl | 3-CH₃-phenyl | phenyl | 8-CH₃ |
| 2-6 | p-phenylene | phenyl | —C₂H₅ | —C₂H₅ | H |
| 2-7 | p-phenylene | phenyl | cyclohexyl | cyclohexyl | H |
| 2-8 | p-phenylene | phenyl | —CH₂-phenyl | —CH₂-phenyl | H |
| 2-9 | p-phenylene | phenyl | phenyl | phenyl | 8-CH₃ |
| 2-10 | 2,5-dimethylphenylene | 4-CH₃-phenyl | 3-CH₃-phenyl | phenyl | H |
| 2-11 | 4,4'-biphenylene | phenyl | —CH₂-phenyl | —CH₂-phenyl | H |
| 2-12 | 4,4'-biphenylene | phenyl | 3-Cl-phenyl | 3-Cl-phenyl | H |

TABLE 2-continued
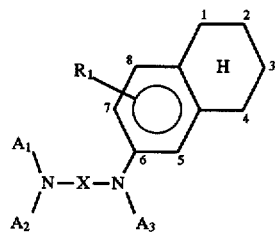
| Comp. No. | X | A₁ | A₂ | A₃ | R₁ |
|---|---|---|---|---|---|
| 2-13 | biphenyl-4,4'-diyl | 4-CH₃-C₆H₄ | 3-CH₃-C₆H₄ | 3-CH₃-C₆H₄ | H |
| 2-14 | biphenyl-4,4'-diyl | 4-CH₃-C₆H₄ | 4-C(CH₃)₃-C₆H₄ | 4-C(CH₃)₃-C₆H₄ | H |
| 2-15 | biphenyl-4,4'-diyl | C₆H₅ | 2-OCH₃-5-CH₃-C₆H₃ | C₆H₅ | H |
TABLE 3
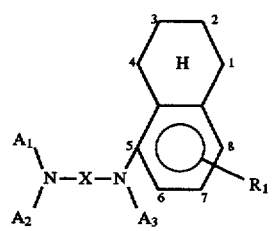
| Comp. No. | X | A₁ | A₂ | A₃ | R₁ |
|---|---|---|---|---|---|
| 3-1 | 3,3'-diCH₃-biphenyl-4,4'-diyl | C₆H₅ | —CH₂—C₆H₅ | —CH₂—C₆H₅ | H |
| 3-2 | 3,3'-diCH₃-biphenyl-4,4'-diyl | C₆H₅ | 3-Cl-C₆H₄ | 3-Cl-C₆H₄ | H |
| 3-3 | 3,3'-diCH₃-biphenyl-4,4'-diyl | 4-CH₃-C₆H₄ | 3-CH₃-C₆H₄ | 3-CH₃-C₆H₄ | H |

TABLE 3-continued

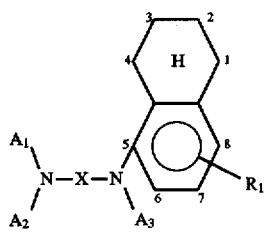

| Comp. No. | X | A₁ | A₂ | A₃ | R₁ |
|---|---|---|---|---|---|
| 3-4 | 3,3'-dimethylbiphenyl | 4-CH₃-phenyl | 4-C(CH₃)₃-phenyl | 4-C(CH₃)₃-phenyl | H |
| 3-5 | 3,3'-dimethylbiphenyl | phenyl | 2-OCH₃-4-CH₃-phenyl | phenyl | H |
| 3-6 | 3,3'-dimethoxybiphenyl | phenyl | 3-Cl-phenyl | 3-Cl-phenyl | 8-CH₃ |
| 3-7 | 3,3'-dimethoxybiphenyl | 4-CH₃-phenyl | 3-CH₃-phenyl | 3-CH₃-phenyl | H |
| 3-8 | 3,3'-dimethoxybiphenyl | 4-CH₃-phenyl | 4-C(CH₃)₃-phenyl | 4-C(CH₃)₃-phenyl | H |
| 3-9 | 3,3'-dimethoxybiphenyl | 4-OCH₃-phenyl | 4-OCH₃-phenyl | phenyl | H |
| 3-10 | 3,3'-dichlorobiphenyl | phenyl | 3-Cl-phenyl | 3-Cl-phenyl | 8-CH₃ |
| 3-11 | 3,3'-dichlorobiphenyl | 4-CH₃-phenyl | 3-CH₃-phenyl | 3-CH₃-phenyl | H |
| 3-12 | 3,3'-dichlorobiphenyl | 4-CH₃-phenyl | 4-C(CH₃)₃-phenyl | 4-C(CH₃)₃-phenyl | H |

TABLE 3-continued

| Comp. No. | X | A₁ | A₂ | A₃ | R₁ |
|---|---|---|---|---|---|
| 3-13 | 3,3'-dichlorobiphenyl-4,4'-diyl | 4-methoxyphenyl | 4-methoxyphenyl | phenyl | H |
| 3-14 | 3-phenylbiphenyl-4,4'-diyl | 3-methylphenyl | 3-methylphenyl | phenyl | 8-CH₃ |
| 3-15 | 3-phenylbiphenyl-4,4'-diyl | 4-methylphenyl | 4-methoxyphenyl | 4-methoxyphenyl | H |

TABLE 4

| Comp. No. | X | A₁ | A₂ | A₃ | R₁ |
|---|---|---|---|---|---|
| 4-1 | 3,3'-dimethylbiphenyl-4,4'-diyl | phenyl | -CH₂-phenyl | -CH₂-phenyl | H |
| 4-2 | 3,3'-dimethylbiphenyl-4,4'-diyl | phenyl | 3-chlorophenyl | 3-chlorophenyl | H |

TABLE 4-continued

| Comp. No. | X | A₁ | A₂ | A₃ | R₁ |
|---|---|---|---|---|---|
| 4-3 | 3,3'-dimethylbiphenyl | 4-CH₃-C₆H₄ | 3-CH₃-C₆H₄ | 3-CH₃-C₆H₄ | H |
| 4-4 | 3,3'-dimethylbiphenyl | 4-CH₃-C₆H₄ | 4-C(CH₃)₃-C₆H₄ | 4-C(CH₃)₃-C₆H₄ | H |
| 4-5 | 3,3'-dimethylbiphenyl | C₆H₅ | 2-OCH₃-4-CH₃-C₆H₃ | C₆H₅ | H |
| 4-6 | 3,3'-dimethoxybiphenyl | C₆H₅ | 3-Cl-C₆H₄ | 3-Cl-C₆H₄ | 8-CH₃ |
| 4-7 | 3,3'-dimethoxybiphenyl | 4-CH₃-C₆H₄ | 3-CH₃-C₆H₄ | 3-CH₃-C₆H₄ | H |
| 4-8 | 3,3'-dimethoxybiphenyl | 4-CH₃-C₆H₄ | 4-C(CH₃)₃-C₆H₄ | 4-C(CH₃)₃-C₆H₄ | H |
| 4-9 | 3,3'-dimethoxybiphenyl | 4-OCH₃-C₆H₄ | 4-OCH₃-C₆H₄ | C₆H₅ | H |
| 4-10 | 3,3'-dichlorobiphenyl | C₆H₅ | 3-Cl-C₆H₄ | 3-Cl-C₆H₄ | 8-CH₃ |
| 4-11 | 3,3'-dichlorobiphenyl | 4-CH₃-C₆H₄ | 3-CH₃-C₆H₄ | 3-CH₃-C₆H₄ | H |

TABLE 4-continued
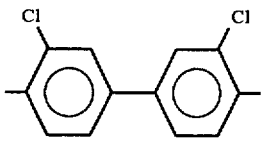
| Comp. No. | X | A₁ | A₂ | A₃ | R₁ |
|---|---|---|---|---|---|
| 4-12 | 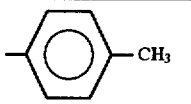 | 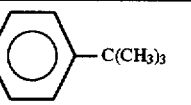 | 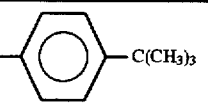 | 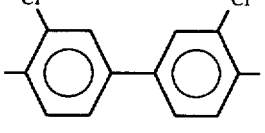 | H |
| 4-13 | 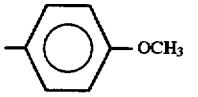 | 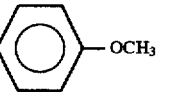 |  | 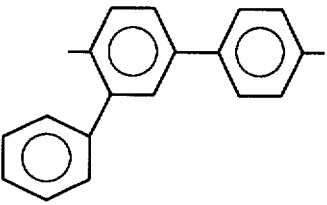 | H |
| 4-14 | 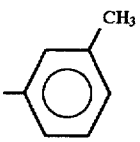 | 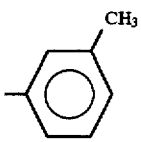 | 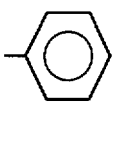 | 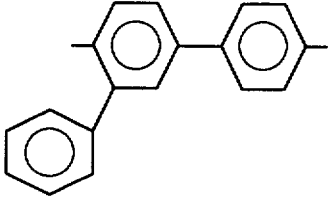 | 8-CH₃ |
| 4-15 | 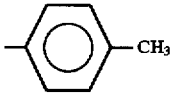 | 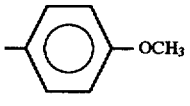 | 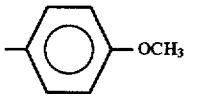 | 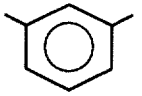 | H |
TABLE 5
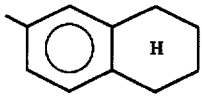
| Comp. No. | X | A₁ | A₂ | A₃ | R₁ |
|---|---|---|---|---|---|
| 5-1 | 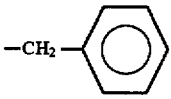 | 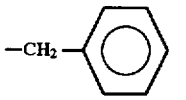 | 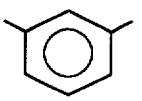 | 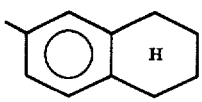 | H |
| 5-2 | 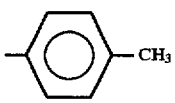 | 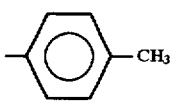 | —⟨⟩—CH₃ | —⟨⟩—CH₃ | H |

TABLE 5-continued

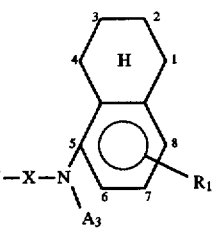

| Comp. No. | X | A₁ | A₂ | A₃ | R₁ |
|---|---|---|---|---|---|
| 5-3 | phenylene | naphthyl | 3-methylphenyl | 3-methylphenyl | H |
| 5-4 | phenylene | naphthyl | 4-biphenyl | 4-biphenyl | H |
| 5-5 | 4,4'-biphenylene | naphthyl | phenyl | phenyl | H |
| 5-6 | 4,4'-biphenylene | naphthyl | 4-methylphenyl | 4-methylphenyl | H |
| 5-7 | 4,4'-biphenylene | naphthyl | 3-methylphenyl | 3-methylphenyl | H |
| 5-8 | 4,4'-biphenylene | naphthyl | 4-methoxyphenyl | 4-methoxyphenyl | H |
| 5-9 | 3,3'-dimethyl-4,4'-biphenylene | naphthyl | phenyl | phenyl | H |
| 5-10 | 3,3'-dimethyl-4,4'-biphenylene | naphthyl | 4-methylphenyl | 4-methylphenyl | H |
| 5-11 | 3,3'-dimethyl-4,4'-biphenylene | naphthyl | 3-methylphenyl | 3-methylphenyl | H |
| 5-12 | 3,3'-dimethyl-4,4'-biphenylene | naphthyl | 4-methoxyphenyl | 4-methoxyphenyl | H |

TABLE 5-continued
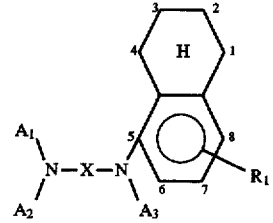
| Comp. No. | X | A₁ | A₂ | A₃ | R₁ |
|---|---|---|---|---|---|
| 5-13 | 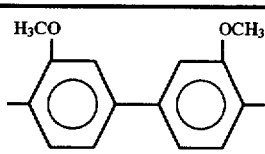 | 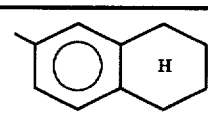 | 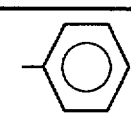 | 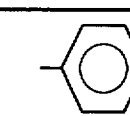 | H |
| 5-14 | 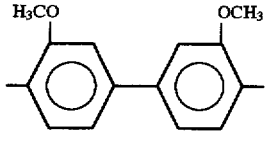 | 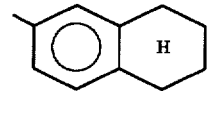 | 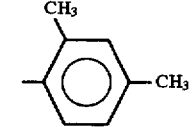 | 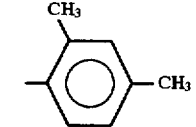 | H |
| 5-15 | 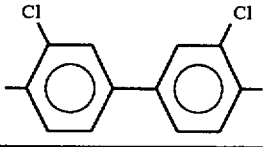 | 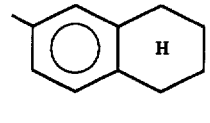 | 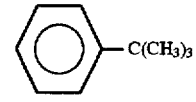 | 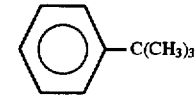 | H |
TABLE 6
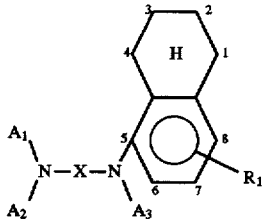
| Comp. No. | X | A₁ | A₂ | A₃ | R₁ |
|---|---|---|---|---|---|
| 6-1 | 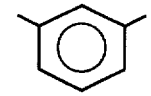 | 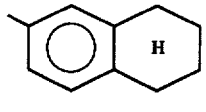 | 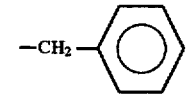 | 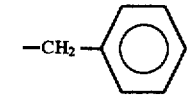 | H |
| 6-2 | 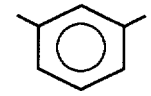 | 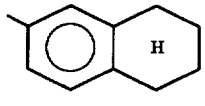 | 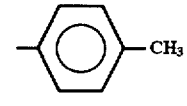 | 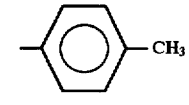 | H |
| 6-3 | 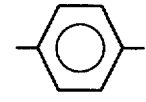 | 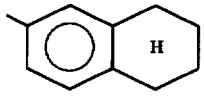 | 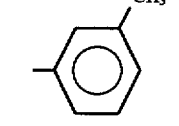 | 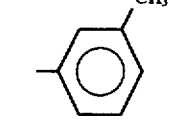 | H |
| 6-4 |  | 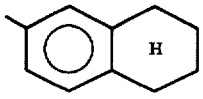 | 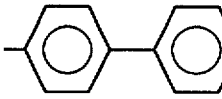 | 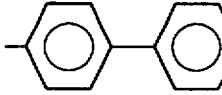 | H |

TABLE 6-continued

| Comp. No. | X | A₁ | A₂ | A₃ | R₁ |
|---|---|---|---|---|---|
| 6-5 | biphenyl | naphthyl (H) | phenyl | phenyl | H |
| 6-6 | biphenyl | naphthyl (H) | 4-CH₃-phenyl | 4-CH₃-phenyl | H |
| 6-7 | biphenyl | naphthyl (H) | 3-CH₃-phenyl | 3-CH₃-phenyl | H |
| 6-8 | biphenyl | naphthyl (H) | 4-OCH₃-phenyl | 4-OCH₃-phenyl | H |
| 6-9 | 3,3'-di-CH₃-biphenyl | naphthyl (H) | phenyl | phenyl | H |
| 6-10 | 3,3'-di-CH₃-biphenyl | naphthyl (H) | 4-CH₃-phenyl | 4-CH₃-phenyl | H |
| 6-11 | 3,3'-di-CH₃-biphenyl | naphthyl (H) | 3-CH₃-phenyl | 3-CH₃-phenyl | H |
| 6-12 | 3,3'-di-CH₃-biphenyl | naphthyl (H) | 4-OCH₃-phenyl | 4-OCH₃-phenyl | H |
| 6-13 | 3,3'-di-OCH₃-biphenyl | naphthyl (H) | phenyl | phenyl | H |
| 6-14 | 3,3'-di-OCH₃-biphenyl | naphthyl (H) | 3,5-di-CH₃-phenyl | 3,5-di-CH₃-phenyl | H |

TABLE 6-continued

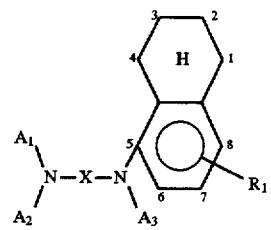

| Comp. No. | X | A₁ | A₂ | A₃ | R₁ |
|---|---|---|---|---|---|
| 6-15 | 3,3'-dichloro-4,4'-biphenylene | tetrahydronaphthyl | 4-t-butylphenyl | 4-t-butylphenyl | H |

TABLE 7

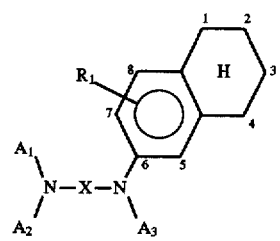

| Comp. No. | X | A₁ | A₂ | A₃ | R₁ |
|---|---|---|---|---|---|
| 7-1 | 1,3-phenylene | tetrahydronaphthyl | $-CH_2$-phenyl | $-CH_2$-phenyl | H |
| 7-2 | 1,3-phenylene | tetrahydronaphthyl | 4-methylphenyl | 4-methylphenyl | H |
| 7-3 | 1,4-phenylene | tetrahydronaphthyl | 3-methylphenyl | 3-methylphenyl | H |
| 7-4 | 1,4-phenylene | tetrahydronaphthyl | 4-biphenylyl | 4-biphenylyl | H |
| 7-5 | 4,4'-biphenylene | tetrahydronaphthyl | phenyl | phenyl | H |
| 7-6 | 4,4'-biphenylene | tetrahydronaphthyl | 4-methylphenyl | 4-methylphenyl | H |

TABLE 7-continued

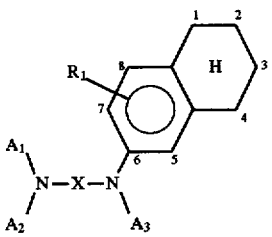

| Comp. No. | X | A₁ | A₂ | A₃ | R₁ |
|---|---|---|---|---|---|
| 7-7 | biphenyl | naphthyl | 4-CH₃-phenyl | 4-CH₃-phenyl | H |
| 7-8 | biphenyl | naphthyl | 4-OCH₃-phenyl | 4-OCH₃-phenyl | H |
| 7-9 | 3,3'-diCH₃-biphenyl | naphthyl | phenyl | phenyl | H |
| 7-10 | 3,3'-diCH₃-biphenyl | naphthyl | 4-CH₃-phenyl | 4-CH₃-phenyl | H |
| 7-11 | 3,3'-diCH₃-biphenyl | naphthyl | 3-CH₃-phenyl | 3-CH₃-phenyl | H |
| 7-12 | 3,3'-diCH₃-biphenyl | naphthyl | 4-OCH₃-phenyl | 4-OCH₃-phenyl | H |
| 7-13 | 3,3'-diOCH₃-biphenyl | naphthyl | phenyl | phenyl | H |
| 7-14 | 3,3'-diOCH₃-biphenyl | naphthyl | 2,4-diCH₃-phenyl | 2,4-diCH₃-phenyl | H |
| 7-15 | 3,3'-diCl-biphenyl | naphthyl | 4-C(CH₃)₃-phenyl | 4-C(CH₃)₃-phenyl | H |

TABLE 8

| Comp. No. | X | (✻) | A₁ | A₂ | A₃ | R₁ |
|---|---|---|---|---|---|---|
| 8-1 | naphthalene-2,6-diyl | 5 | p-tolyl | p-tolyl (CH₃) | p-tolyl (CH₃) | H |
| 8-2 | naphthalene-2,6-diyl | 5 | naphthyl | m-tolyl (CH₃) | m-tolyl (CH₃) | H |
| 8-3 | naphthalene-1,4-diyl | 5 | naphthyl | m-methoxyphenyl (OCH₃) | m-methoxyphenyl (OCH₃) | H |
| 8-4 | naphthalene-1,4-diyl | 6 | naphthyl | biphenyl | biphenyl | H |

TABLE 8-continued

| Comp. No. | X | (X) | A₁ | A₂ | A₃ | R₁ |
|---|---|---|---|---|---|---|
| 8-5 | anthracenyl | 5 | 8-methylnaphthyl | 4-methoxyphenyl | 4-methoxyphenyl | H |
| 8-6 | anthracenyl | 5 | naphthyl | 3,5-dimethylphenyl | phenyl | H |
| 8-7 | 4'-methyl-p-terphenyl | 6 | 3-methylphenyl | 3-methylphenyl | 3-methylphenyl | H |
| 8-8 | 4'-methyl-p-terphenyl | 6 | naphthyl | naphthyl | naphthyl | H |

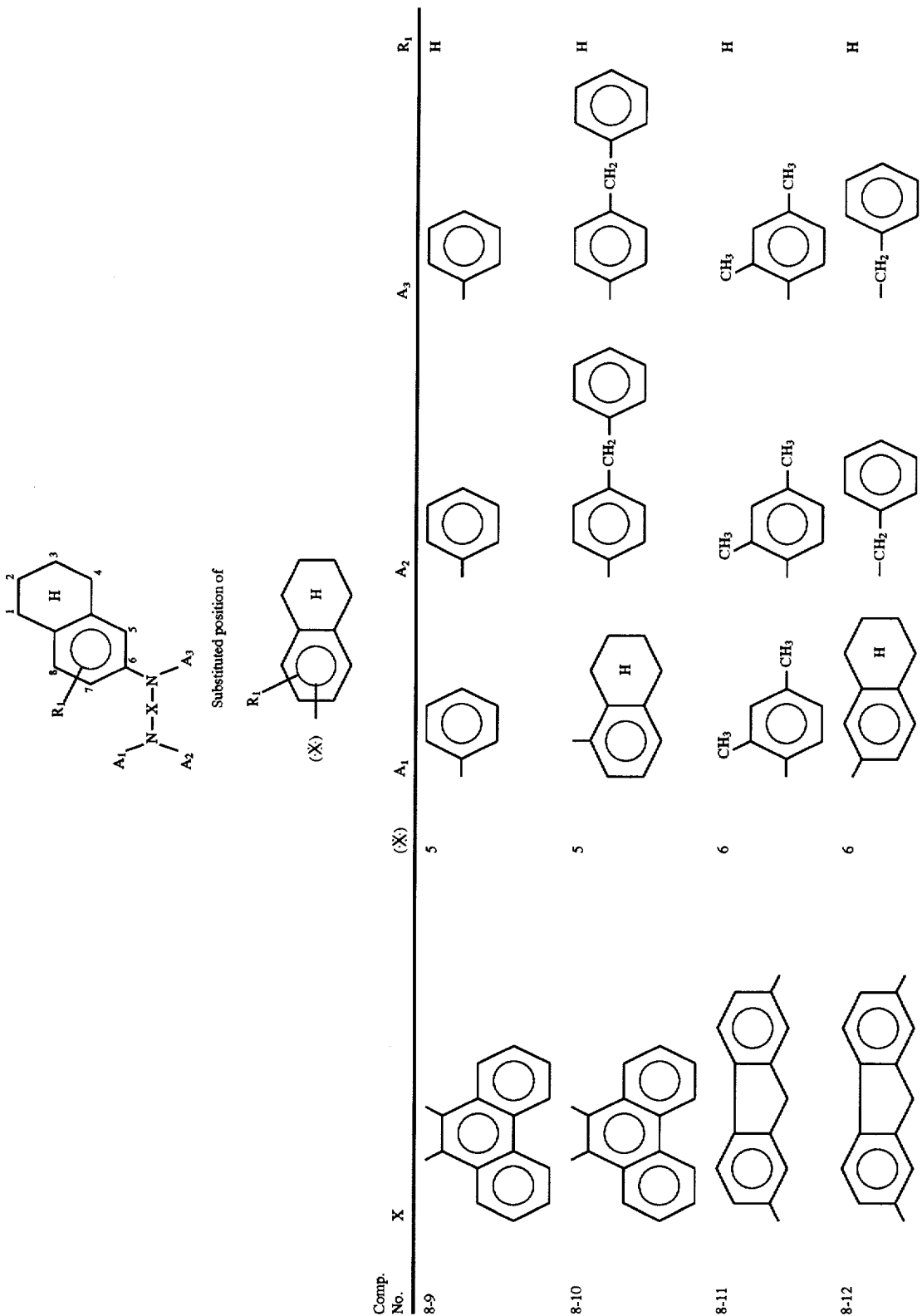

TABLE 8-continued
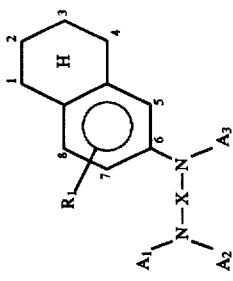
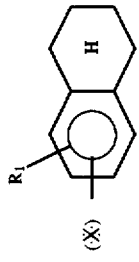
Substituted position of
| Comp. No. | X | (X) | A₁ | A₂ | A₃ | R₁ |
|---|---|---|---|---|---|---|
| 8-13 | ⟨⟩—O—⟨⟩ | 5 | naphthyl | 3-CH₃-phenyl | 3-CH₃-phenyl | H |
| 8-14 | ⟨⟩—S—⟨⟩ | 6 | 4-OCH₃-phenyl | 4-OCH₃-phenyl | 4-OCH₃-phenyl | H |
| 8-15 | ⟨⟩—SO₂—⟨⟩ | 6 | naphthyl | 2-C(CH₃)₃-phenyl | 2-C(CH₃)₃-phenyl | H |

TABLE 9
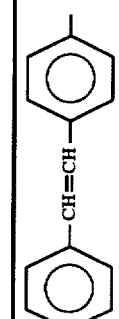

TABLE 9-continued
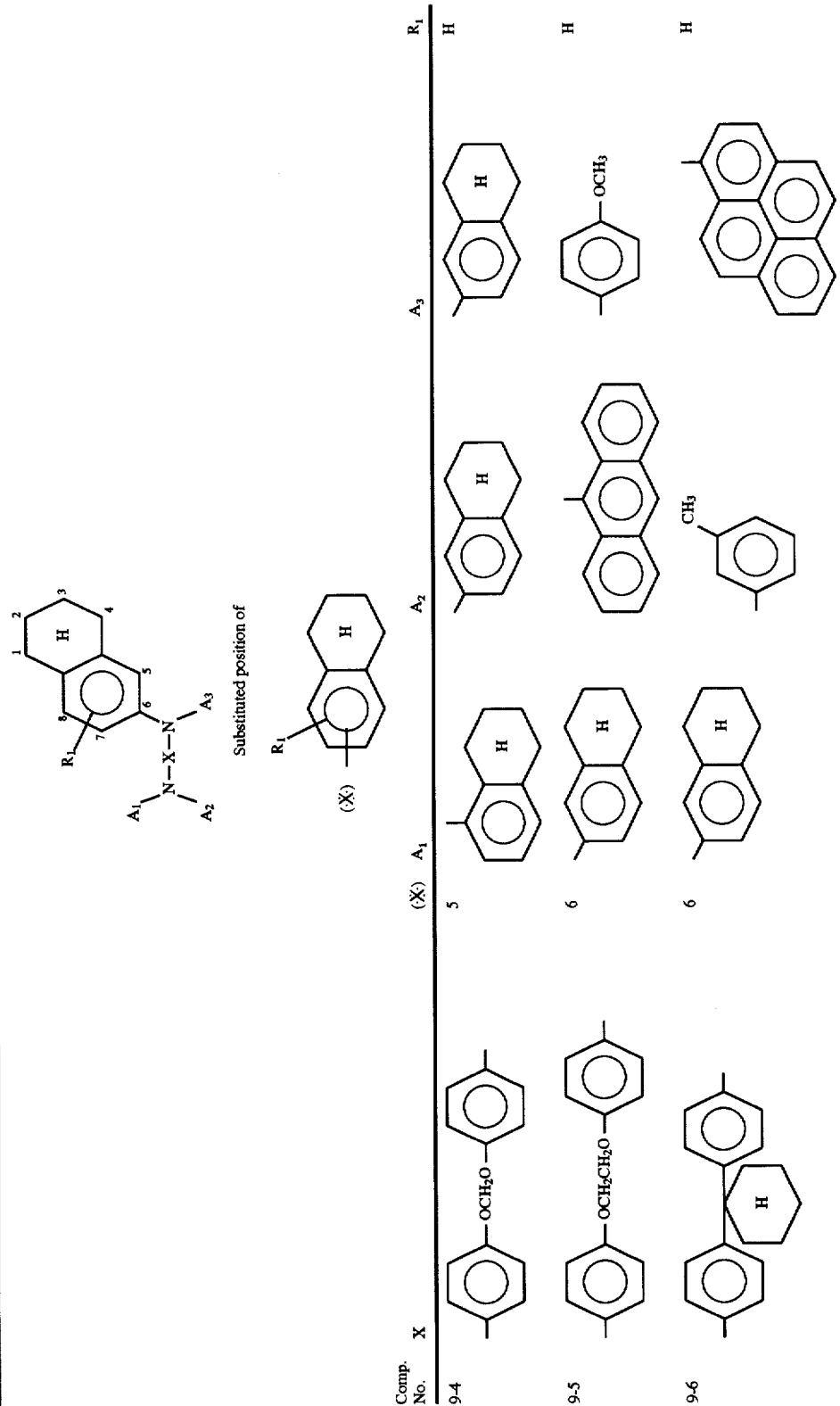

TABLE 9-continued

[Structure: naphthalene-R₁ with N-X-N(A₁,A₂)(A₃) substituent; substituted position of naphthalene ring shown as (X)]

| Comp. No. | X | (X) | A₁ | A₂ | A₃ | R₁ |
|---|---|---|---|---|---|---|
| 9-7 | triphenylmethyl (CH with three phenyl groups, one p-tolyl) | 6 | naphthyl (H) | naphthyl (H) | naphthyl (H) | H |
| 9-8 | 9,9-diphenylfluorene linkage | 5 | naphthyl (H) | p-tolyl (CH₃) | p-tolyl (CH₃) | H |
| 9-9 | N-N with two C=O (diacyl/imide) | 5 | biphenyl | m-tolyl (CH₃) | m-tolyl (CH₃) | H |

TABLE 9-continued

| Comp. No. | X | A₁ | A₂ | A₃ | R₁ |
|---|---|---|---|---|---|
| | | Substituted position of (X) | | | |
| 9-10 | isobenzofuran (with methyl groups) | 6 | phenyl-CH₂CH₂OC₂H₅ | phenyl | phenyl | H |
| 9-11 | dibenzofuran | 5 | naphthyl | 4-ethylbiphenyl | 4-ethylbiphenyl | C₂H₅ |
| 9-12 | dibenzothiophene | 6 | naphthyl | 4-methylphenyl | 4-methylphenyl | H |
| 9-13 | N-ethylcarbazole | 6 | 4-methoxyphenyl | 4-methoxyphenyl | 4-methoxyphenyl | H |

TABLE 9-continued

| Comp. No. | X | A₁ | A₂ | A₃ | R₁ |
|---|---|---|---|---|---|
| 9-14 | (dibenzofuran-like with O, N-phenyl, methyl substituents) | naphthyl (methyl-substituted) | 2-OCH₃, 4-CH₃ phenyl | 2-OCH₃, 4-CH₃ phenyl | H |
| 9-15 | (dibenzothiophene-like with S, N-phenyl, methyl substituents) | naphthyl (methyl-substituted) | 3,5-(CH₃)₂ phenyl | 3,5-(CH₃)₂ phenyl | H |

The electrophotographic photoreceptor of the present invention has a photosensitive layer containing one or more of the above-mentioned diamine compounds. Various forms are available for the photosensitive layer, and any one of them may be employed for the photosensitive layer of the electrophotographic photoreceptor of the present invention. Typical examples of such photoreceptors are shown in FIGS. 1 to 5.

The photoreceptor shown in FIG. 1 is the one wherein a photosensitive layer 2 comprising the diamine compound, a sensitizing dye and a binder, is formed on an electrically conductive support 1.

Figure 2:
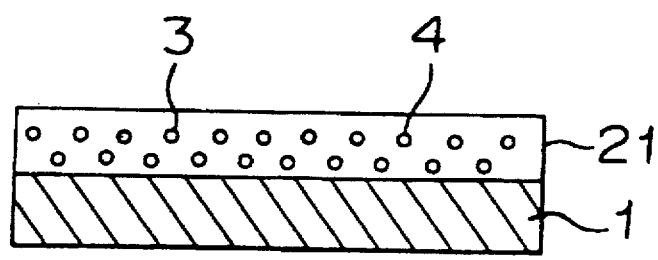
FIG. 2 is a cross-sectional view of a single layer electrophotographic photoreceptor having a charge-generating material dispersed therein.

The photoreceptor shown in FIG. 2 is the one wherein a photosensitive layer 21 having a charge-generating material 4 dispersed in a charge-transporting medium 3 comprising a diamine compound and a binder resin, is formed on an electrically conductive support 1. With this photoreceptor, a charge carrier is generated when the charge-generating material absorbs light, and the charge carrier is transported by the charge-transporting medium. Here, the charge-transporting material should preferably be transparent to the light for generating the charge carrier. The diamine compound of the present invention shows no substantial absorption in a visible wavelength region and thus satisfies a condition that the absorption wavelength region does not overlap with the absorption wavelength region of the charge-generating material.

Figure 3:
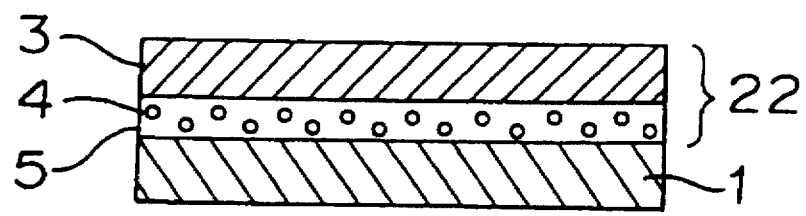
FIG. 3 is a cross-sectional view of a electrophotographic photoreceptor having a charge-generating layer and a charge-transporting layer laminated in this order on an electrically conductive support.

The photoreceptor shown in FIG. 3 is the one wherein a photosensitive layer 22 composed of a lamination of a charge-generating layer 5 containing a charge-generating material 4 as the main component and a charge-transporting layer 3 comprising the diamine compound and a binder rein, is formed on an electrically conductive support 1. With this photoreceptor, light passed through the charge-transporting layer 3 reaches the charge-generating layer 5, whereupon it is absorbed by the charge-generating material 4, whereby a charge carrier is generated. This charge carrier is injected into and transported by the charge-transporting layer 3.

Figure 4:
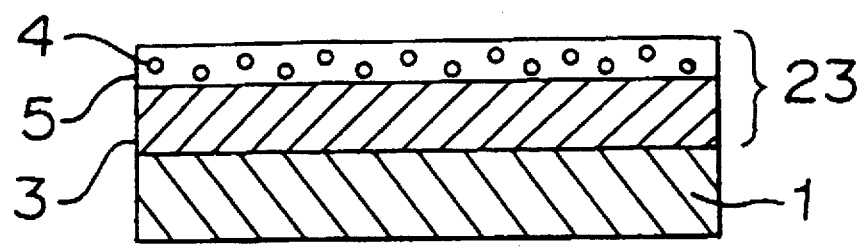
FIG. 4 is a cross-sectional view of a electrophotographic photoreceptor having a charge-transporting layer and a charge-generating layer laminated in this order on an electrically conductive support.

The photoreceptor shown in FIG. 4 is the one wherein a photosensitive layer 23 is formed with the order of lamination of the charge-generating layer 5 and the charge-transporting layer 3 of the photoreceptor in FIG. 3 reversed. The generation and transportation of a charge carrier may be explained by the same mechanism as described above.

Figure 5:
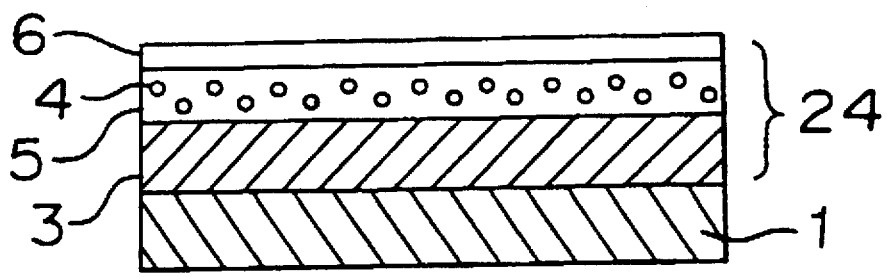
FIG. 5 is a cross-sectional view of a electrophotographic photoreceptor provided with a protective layer.

The photoreceptor shown in FIG. 5 is the one wherein a photosensitive layer 24 is formed with a protective layer 6 further laminated on the charge-generating layer 5 of the photoreceptor of FIG. 4 for the purpose of improving the mechanical strength.

As illustrated in the foregoing, the photoreceptor of the present invention can be prepared by conventional methods. For example, it may be prepared by coating on an electrically conductive support a coating solution prepared by adding a charge-generating material, a sensitizing dye, an electron attractive compound, a plasticizer, a pigment, other additives, as the case requires to a solution having the diamine compound of the formula (1) dissolved in a suitable solvent together with a binder resin, followed by drying to form a photosensitive layer having a thickness of from a few μm to a few tens μm. In the case of a photosensitive layer comprising two layers of a charge-generating layer and a charge-transporting layer, it may be prepared by coating the above coating solution on a charge-generating layer, or by forming a charge-generating layer on a charge-transporting layer obtained by coating the above coating solution. Further, the photoreceptor thus prepared, may further be provided with an adhesive layer, an interlayer or a barrier layer, as the case requires.

The amount of the diamine compound in the photosensitive layer of a single layer type photoreceptor or in a charge-transporting layer of a laminated layer type photoreceptor, is usually from 30 to 70%, preferably from 40 to 60%, by weight.

The solvent to be used for the preparation of the coating solution may, for example, be a polar organic solvent such as tetrahydrofuran, 1,4-dioxane, methyl ethyl ketone, cyclohexanone, acetonitrile, N,N-dimethylformamide or ethyl acetate, an aromatic organic solvent such as toluene or xylene, or a chlorinated hydrocarbon solvent such as dichloromethane or dichloroethane. A solvent providing a good solubility to the diamine compound and the binder resin is preferably employed.

The sensitizing dye may, for example, be a triarylmethane dye such as methyl violet, brilliant green, crystal violet or acid violet, a xanthene dye such as Rhodamine B, Eosine S or Rose Bengale, a thiazine dye such as methylene blue, a pyrylium dye such as a benzopyrylium salt, a thiapyrylium dye, or a cyanine dye.

The electron attractive compound which is capable of forming a charge transfer complex with the diamine compound may, for example, be a quinone such as chloranil, 2,3-dichloro-1,4-naphthoquinone, 1-nitroanthraquinone, 2-chloroanthraquinone or phenanthrenequinone, an aldehyde such as 4-nitrobenzaldehyde, a ketone such as 9-benzoylanthracene, indandione, 3,5-dinitrobenzophenone, 2,4,7-trinitrofluorenone or 2,4,5,7-tetranitrofluorenone, an acid anhydride such as phthalic anhydride or 4-chloronaphthalic anhydride, a cyano compound such as tetracyanoethylene, terephthalal malenonitrile or 9-anthrylmethylidene malenonitrile, or a phthalide such as 3-benzalphthalide, 3-(α-cyano-p-nitrobenzal)-4,5,6,7-tetrachlorophthalide.

As the binder resin, various resins which are compatible with diamine compound may be mentioned including polymers and copolymers of vinyl compounds such as styrene, vinyl acetate, vinyl chloride, an acrylic acid ester, a methacrylic acid ester and butadiene, polyvinyl acetal, polycarbonate, polyester, polyphenylene oxide polyurethane, cellulose ester, a phenoxy resin, a silicone resin, and an epoxy resin. The amount of the binder resin is usually within a range of from 0.4 to 10 parts by weight, preferably from 0.5 to 5 parts by weight, per part by weight of the diamine compound.

Further, the photosensitive layer of the present invention may contain a conventional plasticizer for the purpose of improving the film-forming property, flexibility and mechanical strength. As such a plasticizer, a phthalic acid ester, a phosphoric acid ester, chlorinated paraffin, methyl naphthalene, an epoxy compound or a chlorinated fatty acid ester may, for example, be mentioned.

As the electrically conductive support on which the photosensitive layer is formed, a material which is commonly used for conventional photoreceptors for electrophotography, may be employed. For example, a drum or sheet made of a metal such as aluminum, stainless steel or copper, or a laminate or vapor deposited product of such metals, or a plastic film, a plastic drum, paper or a paper tube treated for electrical conduction by coating a conductive material such as a metal powder, carbon black, copper iodide or a polymer electrolyte together with a proper binder, or a plastic film or plastic drum having electrical conductivity imparted by incorporating a conductive material, may be mentioned.

Now, the present invention will be described in further detail with reference to Examples. However, it should be understood that the present invention is by no means restricted by such specific Examples.

PREPARATION EXAMPLE 1

(Preparation of Compound No. 7-5)

Preparation of iodotetralin 132.2 g (1.00 mol) of tetralin was dissolved in 600 ml of 80% acetic acid, and 101.5 g (0.40 mol) of iodine, 45.5 g (0.20 mol) of periodic acid dihydrate and 15 ml of concentrated sulfuric acid were added thereto. The mixture was heated to 70° C. with stirring. The mixture was further stirred for 3 hours at the same temperature whereupon disappearance of tetralin was confirmed to terminate the reaction. The reaction mixture was added to 1000 ml of water, and the separated oily substance was extracted with 1000 ml of toluene. The toluene layer was washed with water and concentrated and then subjected to distillation under reduced pressure (bp: 120° C./3 mmHg) to obtain 215.3 g of the main fraction (yield: 83.4%). This product was a mixture of 5-iodotetralin and 6-iodotetralin in a blend ratio of 1:2.

Preparation of N-(1,2,3,4-tetrahydronaphtho-6-yl)aniline 171.0 g (0.66 mol) of the iodotetralin mixture prepared as described above, was mixed with 81.0 g (0.60 mol) of acetanilide, 3.8 g (0.06 mol) of copper powder, 103.5 g (0.75 mol) of anhydrous potassium carbonate and 50 ml of nitrobenzene, and the mixture was stirred at 200° C. for 12 hours. Disappearance of acetanilide was confirmed to terminate the reaction. A 120 ml of isoamyl alcohol and an aqueous solution having 84 g (1.27 mol) of 85% potassium hydroxide dissolved in 160 ml of water, was added thereto, and hydrolysis was carried out for 10 hours at a temperature of from 130 to 140° C. After confirming the termination of the hydrolysis, 600 ml of water was added, and nitrobenzene and isoamyl alcohol were distilled off by azeotropic distillation. 1000 ml of toluene was added to the residue to dissolve the product, and the toluene layer was separated. The toluene layer was washed with 500 ml of water and then concentrated, and an oily substance thereby obtained, was subjected to column chromatography (carrier: silica gel, eluent: toluene/hexane =1:1) to carry out separation and purification of the mixture. The fraction of N-(1,2,3,4-tetrahydronaphtho-6-yl)aniline was concentrated to obtain 63.6 g (yield: 47.5%, melting point: 65.0°–66.0° C.) of N-(1,2,3,4-tetrahydronaphtho-6-yl)aniline.

Preparation of N,N'-diphenyl-N,N'-bis(1,2,3,4-tetrahydronaphtho-6-yl)-4,4'-diamino-1,1'-diphenyl (Compound No. 7-5)

53.6 g (0.24 mol) of the N-(1,2,3,4-tetrahydronaphtho-6-yl)aniline prepared as described above, was mixed with 32.5 g (0.08 mol) of 4,4'-diiodo-1,1'-diphenyl, 1.0 g (0.016 mol) of copper powder, 13.8 g (0.10 mol) of anhydrous potassium carbonate and 30 ml of nitrobenzene, and the mixture was stirred at 200° C. for 20 hours. Disappearance of N-(1,2,3,4-tetrahydronaphtho-6-yl)aniline was confirmed to terminate the reaction. 1000 ml of toluene was added thereto to dissolve the product, and the solution was then filtered and concentrated. The concentrated product was purified by column chromatography (carrier: silica gel, eluent: toluene/hexane=1:3) to obtain 36.3 g (yield: 76.0%, melting point: 192.2°–194.3° C.) of N,N'-diphenyl-N,N'-bis(1,2,3,4-tetrahydronaphtho-6-yl)-4,4'-diamino-1,1'-diphenyl.

The results of the elemental analysis as $C_{44}H_{40}N_2$ were as follows. Carbon: 88.99% (88.54%), hydrogen: 6.91% (6.76%), nitrogen: 4.61% (4.70%) (calculated values are shown in brackets).

The wavenumbers ($cm^{-1}$) of characteristic groups of the infrared absorption spectrum (KBr tablet method) were 2922, 1595, 1489, 1275, etc.

PREPARATION EXAMPLE 2

Preparation of N,N'-di(4-tolyl)-N,N'-bis(1,2,3,4-tetrahydronaphtho-6-yl)-4,4'-diamino-1,1'-diphenyl (Compound No. 7-6)

56.96 g (0.24 mol) of N-(1,2,3,4-tetrahydronaphtho-6-yl)-p-toluidine prepared in the same manner as Preparation Example 1 except that in Preparation Example 1, p-acetotoluidide was used instead of acetanilide, was mixed with 32.5 g (0.08 mol) of 4,4'-diiodo-1,1'-diphenyl, 1.0 g (0.016 mol) of copper powder, 13.8 g (0.10 mol) of anhydrous potassium carbonate and 30 ml of nitrobenzene, and the mixture was stirred at 200° C. for 20 hours. Disappearance of N-(1,2,3,4-tetrahydronaphtho-6-yl)-p-toluidine was confirmed to terminate the reaction. 1000 ml of toluene was added thereto to dissolve the product, and the solution was filtered and concentrated. The concentrated product was purified by column chromatography (carrier: silica gel, eluent: toluene/hexane=1/3) to obtain 40.69 g (yield: 81.4%, melting point: 209.5°–210.5° C.) of N,N'-di(4-tolyl)-N,N'-bis(1,2,3,4-tetrahydronaphtho-6-yl)-4,4'-diamino-1,1'-diphenyl.

The results of the elemental analysis as $C_{46}H_{44}N_2$ were as follows. Carbon: 88.32% (88.42%), hydrogen: 7.01% (7.10%), nitrogen: 4.63% (4.48%) (calculated values are shown in brackets).

The wavenumbers ($cm^{-1}$) of characteristic groups of the infrared absorption spectrum (KBr tablet method) were 2920, 1599, 1490, 1269, etc.

PREPARATION EXAMPLE 3

Preparation of N,N'-di(4-tolyl)-N,N'-bis(1,2,3,4-tetrahydronaphtho-5-yl)-4,4'-diamino-1,1'-diphenyl (Compound No. 5-6)

The preparation was carried out in the same manner as in Preparation Example 1 except that in Preparation Example 1, p-acetotoluidide was used instead of acetanilide, whereupon N-(1,2,3,4-tetrahydronaphtho-5-yl)-p-toluidine obtained together with N-(1,2,3,4-tetrahydronaphtho-6-yl)-p-toluidine was separated. 56.96 g (0.24 mol) of N-(1,2,3,4-tetrahydronaphtho-5-yl)-p-toluidine thus obtained, was mixed with 32.5 g (0.08 mol) of 4,4'-diiodo-1,1'-diphenyl, 1.0 g (0.016 mol) of copper powder, 13.8 g (0.10 mol) of anhydrous potassium carbonate and 30 ml of nitrobenzene, and the mixture was stirred at 200° C. for 20 hours. Disappearance of N-(1,2,3,4-tetrahydronaphtho-5-yl)-p-toluidine was confirmed to terminate the reaction. 1000 ml of toluene was added thereto to dissolve the product, and the solution was filtered and concentrated. The concentrated product was purified by column chromatography (carrier: silica gel, eluent: toluene/hexane=1/3) to obtain 38.59 g (yield: 77.2%, melting point: 227.0°–230.0° C.) of N,N'-di(4-tolyl)-N,N'-bis(1,2,3,4-tetrahydronaphtho-5-yl)-4,4'-diamino-1,1'-diphenyl.

The results of the elemental analysis as $C_{46}H_{44}N_2$ were as follows. Carbon: 88.22% (88.42%), hydrogen: 7.21% (7.10%), nitrogen: 4.51% (4.48%) (calculated values are indicated in brackets). The wavenumbers ($cm^{-1}$) of characteristic groups of the infrared absorption spectrum (KBr tablet method) were 2922, 1600, 1486, 1290, etc.

EXAMPLE 1

As a charge-generating material, 1.5 parts by weight of the following Chlorodiane Blue (charge-generating material No. 1):

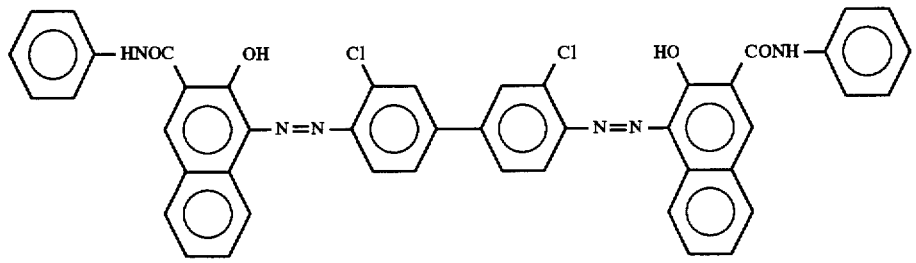

was added to 18.5 parts by weight of a 8% THF solution of a polyester resin (Viron 200, manufactured by Toyobo Co., Ltd.), and the mixture was put in an agate pot containing agate balls and rotated and dispersed for one hour by a planetary pulverizer (manufactured by Fritsch Co.). The obtained dispersion was coated on an aluminum surface of an aluminum-vapor deposited PET film as an electrically conductive support, by means of a wire bar coater and dried for 2 hours at 60° C. under atmospheric pressure and further for 2 hours under reduced pressure to form a charge-generating layer having a thickness of 0.3 µm.

On the other hand, as a charge-transporting material, 1.5 parts by weight of a diamine compound of Compound No. 7-5 was added to 18.75 parts by weight of a 8% dichloroethane solution of a polycarbonate resin (Panlite K-1300, manufactured by Teijin Kasei K.K.), and the mixture was subjected to supersonic waves to completely dissolve the diamine compound. This solution was coated on the above-mentioned charge-generating layer by a wire bar coater and dried for 2 hours at 60° C. under atmospheric pressure and further for 2 hours under reduced pressure to form a charge-transporting layer having a thickness of about 20 µm, to obtain photoreceptor No. 1.

With respect to this photoreceptor, the sensitivity was measured by means of an electrostatic copy paper testing apparatus ("EPA-8100" tradename, manufactured by Kawaguchi Denki Seisakusho K.K.). Firstly, the photoreceptor was electrified by corona discharge of −8 kV in a dark place, and then subjected to exposure with a white light of 3.0 lux, whereby the time (seconds) until the surface potential decreased to one half of the initial surface potential, was measured, to obtain a half value exposure E½ (lux·sec). The initial surface potential of this photoreceptor was −989 V, and E½ was 0.79 lux·sec.

EXAMPLES 2 to 43

Photoreceptors No. 2 to No. 43 were prepared in the same manner as in Example 1 except that the charge-generating material and the charge-transporting material (diamine compound) used in Example 1 were changed to those shown in Tables 10 to 12.

The structures of charge-generating materials No. 2 to No. 4 shown in Tables 10 to 12 will be shown below.

Charge-generating material No. 2

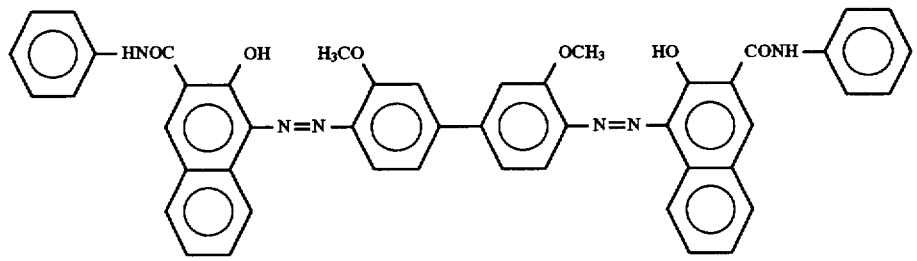

Charge-generating material No. 3

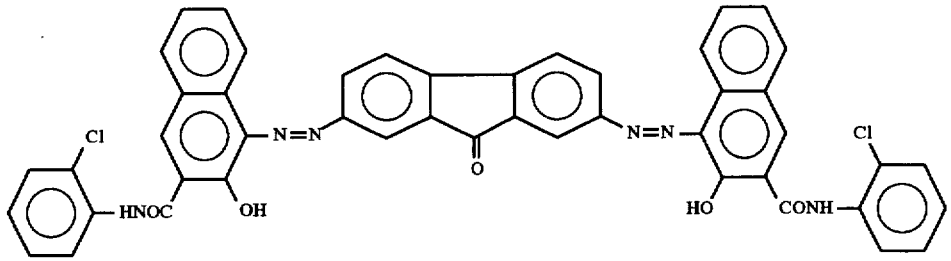

Charge-generating material No. 4

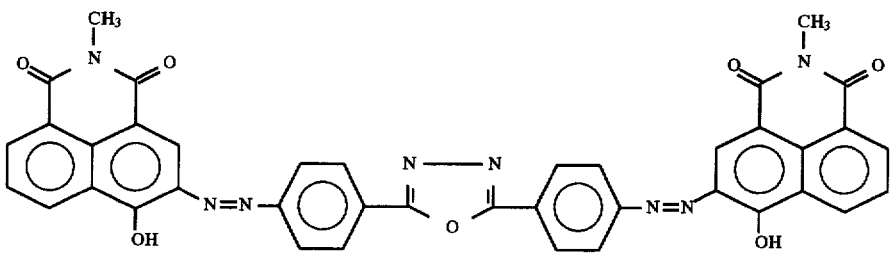

With respect to photoreceptors No. 2 to No. 43, the sensitivities were measured in the same manner as in Example 1. The results are shown in Tables 13 to 15.

TABLE 10

| Example No. | Photo-receptor No. | Charge-transporting material Compound No. | Charge-generating material No. |
|---|---|---|---|
| 2 | 2 | 1-2 | 3 |
| 3 | 3 | 1-4 | 1 |
| 4 | 4 | 1-13 | 1 |
| 5 | 5 | 1-15 | 1 |
| 6 | 6 | 2-2 | 2 |
| 7 | 7 | 2-3 | 2 |
| 8 | 8 | 2-8 | 2 |
| 9 | 9 | 2-13 | 4 |
| 10 | 10 | 2-15 | 1 |
| 11 | 11 | 3-1 | 3 |
| 12 | 12 | 3-4 | 3 |
| 13 | 13 | 3-6 | 4 |
| 14 | 14 | 3-14 | 4 |
| 15 | 15 | 4-3 | 3 |
| 16 | 16 | 4-9 | 3 |
| 17 | 17 | 4-11 | 2 |
| 18 | 18 | 4-15 | 2 |

TABLE 11

| Example No. | Photo-receptor No. | Charge-transporting material Compound No. | Charge-generating material No. |
|---|---|---|---|
| 19 | 19 | 5-1 | 1 |
| 20 | 20 | 5-5 | 3 |
| 21 | 21 | 5-6 | 1 |
| 22 | 22 | 5-8 | 1 |
| 23 | 23 | 5-11 | 1 |
| 24 | 24 | 5-13 | 2 |
| 25 | 25 | 6-5 | 2 |
| 26 | 26 | 6-6 | 2 |
| 27 | 27 | 6-8 | 2 |
| 28 | 28 | 6-10 | 1 |
| 29 | 29 | 6-15 | 3 |
| 30 | 30 | 7-2 | 3 |
| 31 | 31 | 7-5 | 4 |
| 32 | 32 | 7-6 | 4 |
| 33 | 33 | 7-8 | 3 |
| 34 | 34 | 7-9 | 3 |
| 35 | 35 | 7-14 | 3 |

TABLE 12

| Example No. | Photo-receptor No. | Charge-transporting material Compound No. | Charge-generating material No. |
|---|---|---|---|
| 36 | 36 | 8-4 | 1 |
| 37 | 37 | 8-5 | 1 |
| 38 | 38 | 8-7 | 3 |
| 39 | 39 | 8-12 | 3 |
| 40 | 40 | 8-13 | 2 |
| 41 | 41 | 9-4 | 4 |
| 42 | 42 | 9-6 | 4 |
| 43 | 43 | 9-13 | 3 |

TABLE 13

| Photo-receptor No. | Initial surface potential (-volt) | $E\frac{1}{2}$ (lux · sec) |
|---|---|---|
| 2 | 1007 | 0.96 |
| 3 | 982 | 1.01 |
| 4 | 965 | 0.80 |
| 5 | 922 | 0.85 |
| 6 | 926 | 1.02 |
| 7 | 871 | 1.07 |
| 8 | 863 | 1.14 |
| 9 | 890 | 0.82 |
| 10 | 954 | 0.81 |
| 11 | 1035 | 0.78 |
| 12 | 988 | 0.84 |
| 13 | 928 | 0.86 |
| 14 | 913 | 0.89 |
| 15 | 1042 | 0.92 |
| 16 | 1011 | 0.94 |
| 17 | 898 | 1.04 |
| 18 | 914 | 0.83 |

TABLE 14

| Photo-receptor No. | Initial surface potential (-volt) | $E\frac{1}{2}$ (lux · sec) |
|---|---|---|
| 19 | 953 | 1.06 |
| 20 | 999 | 0.85 |
| 21 | 1001 | 0.89 |
| 22 | 948 | 0.90 |
| 23 | 997 | 0.87 |
| 24 | 849 | 0.79 |
| 25 | 904 | 0.84 |
| 26 | 918 | 0.86 |
| 27 | 892 | 0.91 |
| 28 | 975 | 0.83 |
| 29 | 1047 | 1.03 |
| 30 | 990 | 0.99 |
| 31 | 940 | 0.76 |

TABLE 14-continued

| Photo-receptor No. | Initial surface potential (-volt) | E½ (lux · sec) |
|---|---|---|
| 32 | 890 | 0.89 |
| 33 | 1016 | 1.07 |
| 34 | 1024 | 0.78 |
| 35 | 993 | 0.82 |

TABLE 15

| Photo-receptor No. | Initial surface potential (-volt) | E½ (lux · sec) |
|---|---|---|
| 36 | 946 | 1.04 |
| 37 | 972 | 1.10 |
| 38 | 1002 | 1.01 |
| 39 | 1015 | 0.98 |
| 40 | 897 | 0.85 |
| 41 | 869 | 0.83 |
| 42 | 823 | 0.91 |
| 43 | 998 | 1.13 |

EXAMPLE 44

Photoreceptor No. 44 was prepared in the same manner as in Example 1 except that the charge-transporting material (diamine compound) used in Example 1 was changed to a mixture of a diamine compound of Compound No. 7-5 and a diamine compound of Compound No. 5-5 in a weight ratio of 1:1. With respect to this photoreceptor, the sensitivity was measured in the same manner as in Example 1, whereby the initial surface potential was −976V, and E½ was 0.77 lux·sec.

EXAMPLE 45

As a charge-generating material, 1.5 parts by weight of α-TiOPc was added to 50 parts by weight of a 3% THF solution of a polyvinylbutyral resin (Esrec BX-L, manufactured by Sekisui Chemical Co., Ltd.), and the mixture was dispersed for 45 minutes by a supersonic disperser. The obtained dispersion was coated on an aluminum surface of an aluminum-vapor deposited PET film as an electrically conductive support, by means of a wire bar coater and dried for 2 hours at 60° C. under atmospheric pressure and further for 2 hours under reduced pressure to form a charge-generating layer having a thickness of 0.2 μm.

On the other hand, as a charge-transporting material, 1.5 parts by weight of a diamine compound of Compound No. 7-5 was added to 18.75 parts by weight of a 8% dichloroethane solution of a polycarbonate resin (Panlite K-1300, manufactured by Teijin Kasei K.K.), and subjected to supersonic waves to completely dissolve the diamine compound. This solution was coated on the above charge-generating layer by a wire bar coater and dried for 2 hours at 60° C. under atmospheric pressure and further for 2 hours under reduced pressure to form a charge-transporting layer having a thickness of about 20 μm, to obtain a photoreceptor No. 45.

With respect to this photoreceptor, the sensitivity was measured by means of an electrostatic copy paper testing apparatus ("EPA-8100", tradename). Firstly, the photoreceptor was electrified by a corona discharge of −8 kV in a dark place and then subjected to exposure with monochromatic light of 800 nm at a dose of 1.0 μW/cm², whereby the energy until the surface potential decreased to one half of the initial surface potential was determined to obtain a half value exposure E½ (μJ/cm²). The initial surface potential of this photoreceptor was −914 V, and E½ was 0.47 μJ/cm².

EXAMPLE 46

Photoreceptor No. 46 was prepared in the same manner as in Example 45 except that as a charge-generating material, the following trisazo compound:

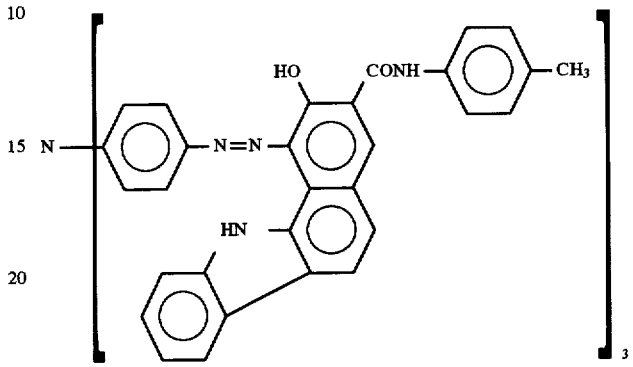

was used instead of α-TiOPc. With respect to this photoreceptor, the sensitivity was measured in the same manner as in Example 45, whereby the initial surface potential was −1005 V, and E½ was 0.50 μJ/cm².

EXAMPLE 47

0.1 part by weight of the following thiapyrylium salt:

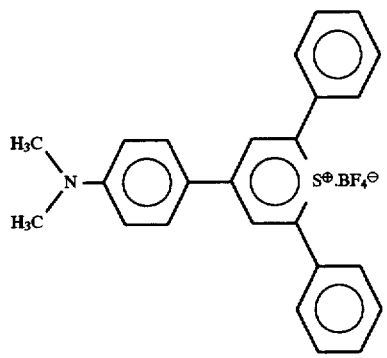

as a charge-generating material and 10 parts by weight of a diamine compound of Compound No. 7-9 as a charge-transporting material were added to 125 parts by weight of a 8% dichloroethane solution of a polycarbonate resin (Panlite K-1300, manufactured by Teijin Kasei K.K.), and supersonic waves were applied to completely dissolve the thiapyrylium salt and the diamine compound. This solution was coated on an aluminum surface of an aluminum-vapor deposited PET film as an electrically conductive support, by means of a wire bar coater and dried for 2 hours at 60° C. under atmospheric pressure and further for 2 hours under reduced pressure to form a photosensitive layer having a thickness of 20 μm, to obtain photoreceptor No. 47.

With respect to this photoreceptor, the sensitivity was measured by means of an electrostatic copy paper testing apparatus ("EPA-8100", tradename). Firstly, the photoreceptor was electrified by a corona discharge of +8 kV in a dark place and then subjected to exposure with a white light of 3.0 lux, whereby the time (seconds) until the initial surface potential decreased to one half, was measured to obtain a half value exposure E½ (lux-sec). The initial surface potential of this photoreceptor was +928 V, and E½ was 1.2 lux·sec.

EXAMPLE 48

The coating solution of a charge-transporting material used in Example 1, was coated on an aluminum surface of an aluminum-vapor deposited PET film by means of a wire bar coater and dried for 2 hours at 60° C. under atmospheric pressure and further for 2 hours under reduced pressure to form a charge-transporting layer having a thickness of 10 μm.

On the other hand, as a charge-generating material, 3.0 parts by weight of the same disazo compound as used in Example 2 was added to 18.5 parts by weight of a 8% THF solution of a polyester resin (Viron 200, manufactured by Toyobo Co., Ltd.), and the mixture was put into an agate pot containing agate balls and rotated and dispersed for one hour by a planetary pulverizer (manufactured by Fritsch Co.). To this dispersion, 200 parts by weight of THF was added, followed by stirring to obtain a coating solution. This coating solution was spray-coated on the above charge-transporting layer and dried for 2 hours at 60° C. under atmospheric pressure and further for 2 hours under reduced pressure to form a charge-generating layer having a thickness of 0.5 μm. Further, a solution having an alcohol-soluble polyamide resin dissolved in isopropanol, was spray-coated on this charge-generating layer and dried for 2 hours at 60° C. under atmospheric pressure and further for 2 hours under reduced pressure to form an overcoating layer having a thickness of 0.5 μm, to obtain photoreceptor No. 48.

With respect to this photoreceptor, the sensitivity was measured in the same manner as in Example 1. The initial surface potential of this photoreceptor was +820 V, and E½ was 1.3 lux·sec.

Novel diamine compounds of the present invention have an excellent charge-transporting ability, and the electrophotographic photoreceptor of the present invention having a photosensitive layer containing such a compound on an electrically conductive support, shows excellent properties as a photoreceptor, such as high sensitivity and high durability and thus has a merit that it can widely be used as a electrophotographic photoreceptor.

What is claimed is:

1. A electrophotographic photoreceptor comprising an electrically conductive substrate having a photosensitive layer thereon which contains a binder resin, a charge generating material or a sensitizing dye, and a diamine compound of the following formula (1):

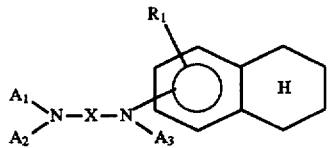
(1)

wherein $R_1$ is a hydrogen atom, a $C_{1-4}$ alkyl group or a $C_{1-4}$ alkoxy group, each of $A_1$, $A_2$ and $A_3$ which are independent of one another, is a substituted or unsubstituted alkyl group, a substituted or unsubstituted aryl group, or a group of the following formula (2):

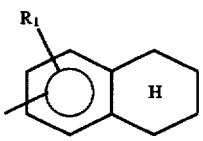
(2)

wherein $R_1$ is as defined above, and X is a substituted or unsubstituted arylene group or a substituted or unsubstituted heterocyclic bivalent group, and wherein the substituent for the substituted alkyl group for each of $A_1$, $A_2$ and $A_3$ is a $C_{1-4}$ alkoxy group which may be substituted by a $C_{1-4}$ alkoxy group or a halogen atom, a $C_{5-6}$ cycloalkyl group, a benzyl or phenyl group which may be substituted by a $C_{1-4}$ alkyl group, a $C_{1-4}$ alkoxy group or a halogen atom; the substituent for the substituted aryl group for each of $A_1$, $A_2$ and $A_3$ is a $C_{1-4}$ alkyl or alkoxy group which may be substituted by a $C_{1-4}$ alkoxy group or a halogen atom, a $C_{5-6}$ cycloalkyl group, a benzyl or phenyl group which may be substituted by a $C_{1-4}$ alkyl or alkoxy group or a halogen atom, or a halogen atom; and the substituent for the substituted arylene or heterocyclic bivalent group for X is the some as the above-identified substituent for the substituted aryl group for each of $A_1$, $A_2$ and $A_3$.

2. The electrophotographic photoreceptor according to claim 1, wherein the diamine compound is represented by the following formula:

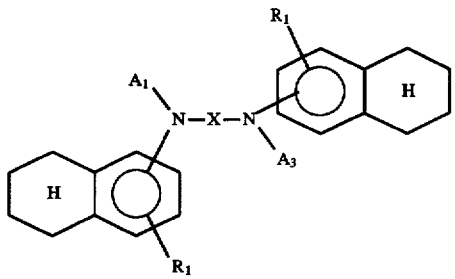

wherein $R_1$, $A_1$, $A_3$ and X are as defined above.

3. The electrophotographic photoreceptor according to claim 1, wherein the diamine compound is represented by the following formula:

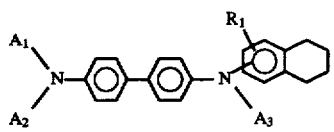

wherein $R_1$, $A_1$, $A_2$ and $A_3$ are as defined above.

4. The electrophotographic photoreceptor according to claim 1, wherein the diamine compound is represented by the following formula:

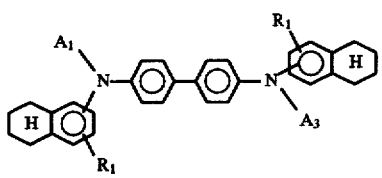

wherein $R_1$, $A_1$ and $A_3$ are as defined above.

5. The electrophotographic photoreceptor according to claim 1, wherein the diamine compound is represented by the following formula:

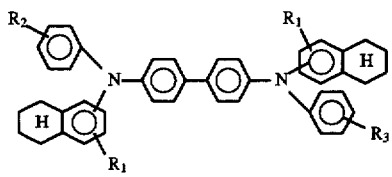

wherein $R_1$ is as defined above, and each of $R_2$ and $R_3$ which are independent of each other, is a hydrogen atom, a $C_{1-4}$ alkyl group or a $C_{1-4}$ alkoxy group.

6. The electrophotographic photoreceptor according to claim 1, wherein the arylene group for X is phenylene, biphenylene, terphenylene, naphthylene, anthrylene, phenanthrylene, fluorene-diyl or a group of the following formula (12):

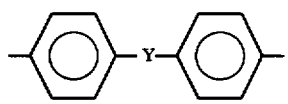 (12)

wherein Y is —O—, —S—, —SO$_2$—, —CH=CH—, —CH$_2$—, —CH$_2$CH$_2$—, —OCH$_2$O—, —OCH$_2$CH$_2$O—,

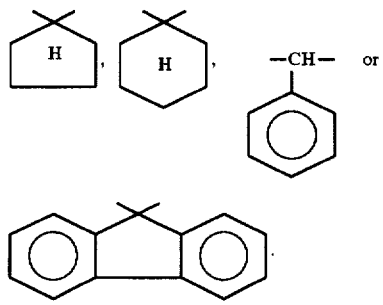

7. The electrophotographic photoreceptor according to claim 1, wherein the heterocyclic ring for the heterocyclic bivalent group for X is oxadiazole, thiadiazole, benzofuran, benzothiophene, benzoxazole, benzothiazole, dibenzofuran, dibenzothiophene, carbazole, acridine, phenazine, phenoxazine or phenothiazine.

* * * * *